US00PP35383P3

(12) United States Plant Patent
Bisschop et al.

(10) Patent No.: US PP35,383 P3
(45) Date of Patent: Sep. 12, 2023

(54) ***HELLEBORUS* PLANT NAMED 'ET EPB 731'**

(50) Latin Name: ***Helleborus orientalis* X *Helleborus ericsmithii***
Varietal Denomination: ET EPB 731

(71) Applicant: ETERNAL PLANT BOIJL B.V., Boijl (NL)

(72) Inventors: Elisabeth Bisschop, Boijl (NL); Bart Noordhuis, Boijl (NL)

(73) Assignee: ETERNAL PLANT BOIJL B.V., Boijl (NL)

( * ) Notice: Subject to any disclaimer, the term of this patent is extended or adjusted under 35 U.S.C. 154(b) by 14 days.

(21) Appl. No.: 17/992,289

(22) Filed: Nov. 22, 2022

(65) Prior Publication Data

US 2023/0165176 P1 May 25, 2023

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./439
See application file for complete search history.

*Primary Examiner* — Susan McCormick Ewoldt
(74) *Attorney, Agent, or Firm* — C. Anne Whealy

(57) ABSTRACT

A new and distinct cultivar of *Helleborus* plant named 'ET EPB 731', characterized by its upright plant habit; moderately vigorous to vigorous growth habit; continuous and freely flowering habit; relatively large light pink and purplish red bi-colored flowers that are held above the foliar plane on relatively long peduncles; and good garden performance.

2 Drawing Sheets

Figure 1:
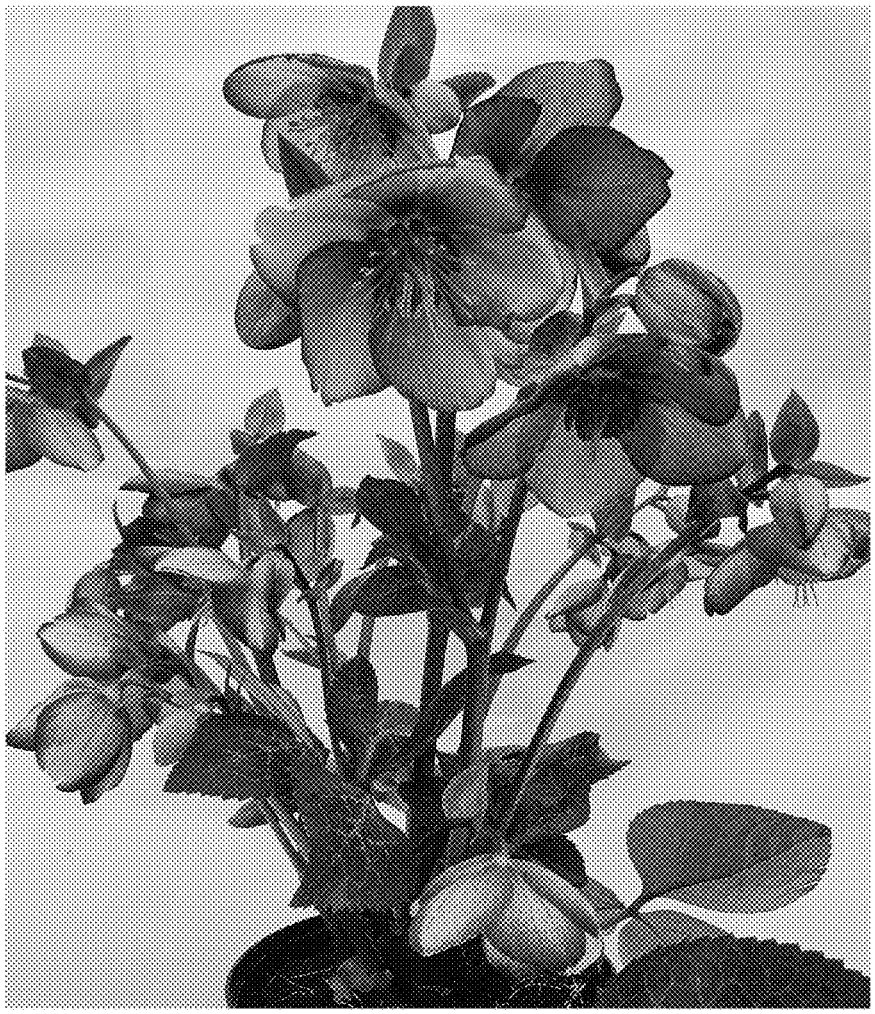

Botanical designation: *Helleborus orientalis* X *Helleborus ericsmithii.*

Cultivar denomination: 'ET EPB 731'.

CROSS-REFERENCED TO CLOSELY-RELATED APPLICATIONS

An European Community Plant Breeder's Rights application for the instant plant was filed by the Assignee, Eternal Plant Boijl B.V. of Boijl, The Netherlands on Nov. 23, 2021, application number 2021/3003. Foreign priority is claimed to this application.

BACKGROUND OF THE INVENTION

The present invention relates to a new and distinct cultivar of *Helleborus* plant, botanically known as *Helleborus orientalis* X *Helleborus ericsmithii* and hereinafter referred to by the name 'ET EPB 731'.

The new *Helleborus* plant is a product of a planned breeding program conducted by the Inventors in Boijl, The Netherlands. The objective of the breeding program was to create new freely-flowering *Helleborus* plants with strong peduncles that hold attractive flowers above the foliar plane.

The new *Helleborus* plant originated from a cross-pollination conducted by the Inventors in Boijl, The Netherlands in February, 2016 of a proprietary selection of *Helleborus orientalis* identified as code number 314A, as the female, or seed, parent, not patented, with a proprietary selection of *Helleborus ericsmithii* identified as code number 989A, as the male, or pollen, parent, not patented. The new *Helleborus* plant was discovered and selected by the Inventors as a single flowering plant from within the progeny of the stated cross-pollination grown in a controlled greenhouse environment in Boijl, The Netherlands in February, 2018.

Asexual reproduction of the new *Helleborus* plant by meristem culture in a controlled greenhouse environment in Boijl, The Netherlands since May, 2018, has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype of the new *Helleborus* plant may vary somewhat with variations in environmental conditions such as temperature and light intensity without, however, any variance in genotype of the new *Helleborus* plant.

The following traits have been repeatedly observed and are determined to be the unique characteristics of 'ET EPB 731'. These characteristics in combination distinguish 'ET EPB 731' as a new and distinct *Helleborus* plant:

1. Upright plant habit.
2. Moderately vigorous to vigorous growth habit.
3. Continuous and freely flowering habit.
4. Relatively large light pink and purplish red bi-colored flowers that are held above the foliar plane on relatively long peduncles.
5. Good garden performance.

Plants of the new *Helleborus* differ from plants of the female parent selection in the following characteristics:

1. Plants of the new *Helleborus* have more durable leaves than plants of the female parent selection.
2. Plants of the new *Helleborus* flower earlier than plants of the female parent selection.
3. Flowers of plants of the new *Helleborus* are larger than flowers of plants of the female parent selection.

4. Peduncles of plants of the new *Helleborus* are stronger than peduncles of plants of the female parent selection.

Plants of the new *Helleborus* differ from plants of the male parent selection in the following characteristics:

1. Leaves of plants of the new *Helleborus* are longer than leaves of plants of the male parent selection.
2. Plants of the new *Helleborus* flower earlier than plants of the male parent selection.
3. Flowers of plants of the new *Helleborus* are larger than flowers of plants of the male parent selection.
4. Peduncles of plants of the new *Helleborus* are stronger and thicker than peduncles of plants of the male parent selection.

Plants of the new *Helleborus* can be compared to plants of *Helleborus* x *hybridus* 'EPB 29', disclosed in U.S. Plant Pat. No. 28,010. In side-by-side comparisons, plants of the new *Helleborus* differ from plants of 'EPB 29' in the following characteristics:

1. Plants of the new *Helleborus* are taller and broader than plants of 'EPB 29'.
2. Plants of the new *Helleborus* are more freely flowering than plants of 'EPB 29'.
3. Flower margins of plants of the new *Helleborus* are darker purplish red in color than flower margins of plants of 'EPB 29'.
4. Peduncles of plants of the new *Helleborus* are longer than peduncles of plants of 'EPB 29'.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1) is a side perspective view of a typical flowering plant of 'ET EPB 731' grown in a container.

Figure 2:
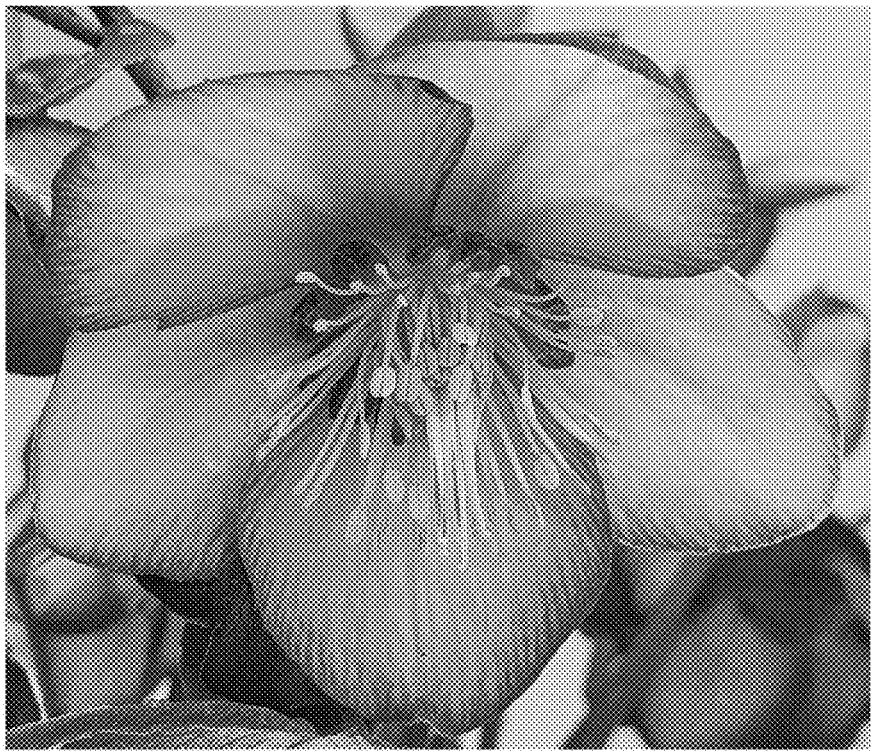

The photograph on the second sheet (FIG. 2) is a close-up view of a typical flower of 'ET EPB 731'.

DETAILED BOTANICAL DESCRIPTION

The aforementioned photographs and following observations, measurements and values describe plants grown during the winter in two-liter containers in an outdoor nursery in Boijl, The Netherlands and under cultural practices typical of commercial *Helleborus* production. During the production of the plants, day temperatures ranged from 0° C. to 10° C. and night temperatures ranged from −15° C. to 0° C. Plants were one year old when the photographs and the description were taken. In the following description, color references are made to The Royal Horticultural Society Colour Chart, 2001 Edition, except where general terms of ordinary dictionary significance are used.

Botanical classification: *Helleborus orientalis* X *Helleborus ericsmithii* 'ET EPB 731'.

Parentage:

*Female, or seed, parent*.—Proprietary selection of *Helleborus orientalis* identified as code number 314A, not patented.

*Male, or pollen, parent*.—Proprietary selection of *Helleborus ericsmithii* identified as code number 989A, not patented.

Propagation:

*Type*.—By meristem culture.

*Time to initiate roots, summer*.—About 15 days at temperatures about 22° C. to 25° C.

*Time to initiate roots, winter*.—About 15 to 22 days at temperatures about 5° C. to 10° C.

*Time to produce a rooted young plant, summer*.—About two months at temperatures about 20° C.

*Time to produce a rooted young plant, winter*.—About 55 to 60 days at temperatures about 12° C. to 15° C.

*Root description*.—Fleshy, vigorous; typically white to brown in color, actual color of the roots is dependent on substrate composition, water quality, fertilizer type and formulation, substrate temperature and physiological age of roots.

*Rooting habit*.—Freely branching; moderately dense.

Plant description:

*Plant and growth habit*.—Herbaceous perennial; upright plant habit with flowers held above the foliar plane; moderately vigorous to vigorous growth habit and moderate growth rate.

*Plant height*.—About 50 cm to 55 cm.

*Plant diameter* (*area of spread*).—About 30 cm to 40 cm.

*Stems*.—Strength: Strong. Aspect: Mostly upright. Texture and luster: Smooth, glabrous; glossy. Color: Close to 146B densely covered with spots, close to 187B.

Leaf description:

*Arrangement*.—Leaves arranged alternately in a basal rosette; leaves palmately compound with three to five leaflets per leaf.

*Leaflet length*.—About 15 cm.

*Leaflet width*.—About 7 cm.

*Leaflet shape*.—Obovate.

*Leaflet apex*.—Obtuse.

*Leaflet base*.—Acute.

*Leaflet margin*.—Serrate.

*Leaflet texture and luster, upper surface*.—Smooth, glabrous; leathery; glossy.

*Leaflet texture and luster, lower surface*.—Smooth, glabrous; leathery; slightly glossy.

*Leaflet venation pattern*.—Pinnate.

*Leaflet color*.—Developing leaves, upper surface: Close to 136B; center and near the midvein, marbled with close to 139D. Developing leaves, lower surface: Close to 148B slightly tinged with close to 187A. Fully expanded leaves, upper surface: Close to 136B marbled with close to 139C to 139D; venation, close to 139C to 139D and proximally, close to 187A. Fully expanded leaves, lower surface: Close to 147B slightly tinged with close to 187A; venation, close to 137B.

*Petioles*.—Length, fully expanded leaves: About 15 cm to 20 cm. Diameter, fully expanded leaves: About 5 mm to 7 mm. Texture, upper and lower surfaces: Smooth, glabrous. Color, upper and lower surfaces: Close to 146A; densely covered with spots, close to N199A.

Flower description:

*Flower shape and habit*.—Single rotate flowers arranged in loosely branched cymes; freely flowering habit with typically about 20 to 30 flowers developing per cyme and up to 45 flowers developing per cyme in the second year of growth; flowers facing outwardly to somewhat drooping.

*Fragrance*.—None detected.

*Natural flowering season*.—Plants begin flowering about two months after planting; plants flower from January through March in The Netherlands.

*Flower longevity on the plant*.—About two months; flowers persistent.

*Inflorescence height*.—About 30 cm to 40 cm.

*Inflorescence diameter*.—About 30 cm to 40 cm.

*Flower buds*.—Length: About 1 cm to 3 cm. Diameter: About 1 cm to 2 cm. Shape: Ovoid. Color: Close to N77B.

*Flower diameter*.—About 6 cm to 8 cm.

*Flower depth* (*height*).—About 2 cm to 4 cm.

*Petals*.—None observed; transformed into nectaries.

*Sepals*.—Quantity and arrangement: Five arranged in a single whorl; slightly imbricate. Length: About 3 cm to 4 cm. Width: About 3 cm to 3.5 cm. Shape: Ovate to obovate. Apex: Obtuse and occasionally emarginate. Base: Rounded. Margin: Mostly entire and occasionally emarginate. Texture and luster, upper and lower surfaces: Smooth, glabrous; matte. Color: When opening and fully opened, upper surface: Close to 69D; towards the margins, close to 71A; color does not change with subsequent development. When opening and fully opened, lower surface: Close to 69D; towards the margins, close to 71A; color does not change with subsequent development.

*Peduncles*.—Length: About 15 cm to 25 cm. Diameter: About 5 mm to 10 mm. Strength: Strong. Aspect: Mostly upright. Texture: Smooth, glabrous. Color: Close to 146B heavily covered with spots, close to 59A.

*Pedicels*.—Length: About 6 cm to 12 cm. Diameter: About 3 mm to 4 mm. Aspect: About 10° from peduncle axis. Strength: Strong. Texture: Smooth, glabrous. Color: Close to 59A.

*Reproductive organs*.—Stamens: Quantity per flower: About 40 to 50. Filament length: About 2 cm. Filament color: Close to 155A. Anther shape: Ovate. Anther length: About 2 mm. Anther color: Close to 157B. Pollen amount: Scarce. Pollen color: Close to 157B. Pistils: Quantity per flower: About five to seven. Pistil length: About 2 cm. Stigma shape: Club-shaped. Stigma color: Close to 157B. Style length: About 1.5 cm. Style color: Close to 193C with stripes, close to 71A. Ovary color: Close to 145A.

*Nectaries*.—Quantity per flower: About 10 to 15. Length: About 5 mm to 8 mm. Width: About 3 mm to 5 mm. Shape: Funnelform. Color: Close to N144D with stripes, close to 71A.

*Seeds and fruits*.—To date, seed and fruit development have not been observed on plants of the new *Helleborus*.

Garden performance: Plants of the new *Helleborus* have been observed to have good garden performance and to tolerate rain, wind and temperatures ranging from about −10° C. to about 35° C.

Pathogen & pest resistance: To date, plants of the new *Helleborus* have not been observed to be resistant to pathogens and pests common to *Helleborus* plants.

It is claimed:

1. A new and distinct *Helleborus* plant named 'ET EPB 731' as illustrated and described.

* * * * *